United States Patent [19]

Hogenmuller et al.

[11] Patent Number: 4,929,662

[45] Date of Patent: May 29, 1990

[54] PROCESS FOR THE PREPARATION OF POLYMER PARTICLES POSSESSING, IMPLANTED ON THEIR SURFACE, AMPHOPHILIC MOLECULES CARRYING ION-FORMING OR REACTIVE GROUPS, AND A PROCESS FOR THE PREPARATION OF A LATEX COMPRISING THESE PARTICLES

[75] Inventors: Roger Hogenmuller, Sainte Foy les Lyon; Bernard Chauvel, Ermont; Jean-Claude Daniel, Fontenay/Sous/Bois, all of France

[73] Assignee: Rhone-Poulenc Chimie, Courbevoie, France

[21] Appl. No.: 191,176

[22] Filed: May 6, 1988

[30] Foreign Application Priority Data

May 11, 1987 [FR] France .................................. 87 06550

[51] Int. Cl.$^5$ ................................................. C08K 5/06
[52] U.S. Cl. ......................................... 524/376; 524/217; 524/302; 524/555; 524/556; 524/567; 524/571; 523/205; 523/207; 526/302; 526/310; 526/311; 526/217; 526/292.3
[58] Field of Search ................ 523/205, 207; 524/376, 524/217, 302; 526/302, 310, 311, 217, 292.3

[56] References Cited

U.S. PATENT DOCUMENTS 2,461,920 2/1949 Pratt .
4,157,323 1/1979 Yen et al. .
4,217,344 8/1980 Vanlerberghe et al. .............. 424/63
4,358,388 11/1982 Daniel et al. .

OTHER PUBLICATIONS

Kirk–Othmer, Encyclopedia of Chemical Technology, 3rd Ed., vol. 8, pp. 910–912.

Primary Examiner—Joseph L. Schofer
Assistant Examiner—Mark D. Sweet
Attorney, Agent, or Firm—Finnegan, Henderson, Farabow, Garrett and Dunner

[57] ABSTRACT

Polymer particles possessing, implanted on their surface, amphiphilic molecules carrying ion-forming or reactive groups, and dispersions thereof, prepared by diffusing, into a previously prepared aqueous seeding dispersion of polymer particles, an organosoluble polymerization initiator, swelling the particles of the dispersion thus obtained by introducing a monomer composition comprising at least one monomer and at least one amphiphilic compound, and polymerizing the monomer composition.

19 Claims, No Drawings

PROCESS FOR THE PREPARATION OF POLYMER PARTICLES POSSESSING, IMPLANTED ON THEIR SURFACE, AMPHOPHILIC MOLECULES CARRYING ION-FORMING OR REACTIVE GROUPS, AND A PROCESS FOR THE PREPARATION OF A LATEX COMPRISING THESE PARTICLES

The present invention relates to a process for the preparation of polymer particles, as such or in aqueous dispersion, which possess, implanted on their surface, amphiphilic molecules carrying ion-forming or reactive groups. The particles or particle latices thus obtained are particularly useful in biological applications.

The polymer particles of the invention carry ion-forming or reactive groups sufficiently distant from the surface of the particles so as to be able to fix, onto these groups, bulky molecules such as proteins without danger of modifying the activity of the bulky molecules by contact with the macromolecular surface.

The process of the invention comprises the following steps:

(1) diffusing, into a previously prepared aqueous seeding dispersion of polymer particles, an organosoluble polymerization initiator having a solubility in water on the order of $10^{-3}$ to $10^{-2}$ g/liter of water, the diffusion being carried out at a temperature below the decomposition temperature of the initiator;

(2) swelling the particles of the dispersion thus obtained by introducing a monomer composition, the monomer composition comprising at least one monomer and at least one amphiphilic compound having an HLB greater than or equal to 10 and a molecular weight greater than or equal to 400, wherein the hydrophilic block of the amphiphilic compound is a hydrophilic oligomer block terminated by at least one ion-forming or reactive group, the swelling being carried out with a quantity of monomer composition less than the maximum quantity of monomer composition which the seeding dispersion can absorb, at a temperature below the decomposition temperature of the initiator; and (3) polymerizing the at least one monomer of the monomer composition at a temperature at least equal to the decomposition temperature of the initiator, the nature of the seeding polymer and the nature of the at least one monomer of the monomer composition being such that the final polymer has a glass transition temperature Tg above about 40° C., and preferably above about 70° C.

Preferably, any amphiphilic compound not implanted on the surface of the aqueous dispersion particles thus obtained is then removed.

Optionally, the polymer particles obtained, possessing molecules of the amphiphilic compound implanted on their surface, are isolated.

The monomer or monomers of the monomer composition, and the monomer or monomers from which the particles of the aqueous seeding dispersion are derived, may be identical or different.

They may be chosen from:
vinylaromatic monomers (such as styrene and vinyltoluene);
alkyl esters of $\alpha,\beta$-unsaturated acids (such as methyl- and ethyl- acrylates and methacrylates); unsaturated esters of carboxylic acids (such as vinyl acetate);
vinyl chloride and vinylidene chloride; dienes (such as butadiene); and monomers possessing nitrile functional groups (such as acrylonitrile).

The aqueous seeding dispersion employed in the first step preferably has a solids content on the order of from 1 to 40% by weight, more preferably on the order of from 10 to 35% by weight. The dispersion comprises polymer particles having a diameter preferably on the order of 0.1 to 15 microns, and most preferably on the order of 0.3 to 5 microns. The particles may correspond to a certain size distribution, or may be calibrated. The term "calibrated" is used herein to denote particles having a uniform particle size, such as those with a standard deviation of the diameter of less than about 5%.

The seeding polymer (expressed as solids) may represent from 50 to 95% by weight, preferably from 65 to 85% by weight, of the final polymer.

A preferred embodiment of the process of the invention comprises employing aqueous seeding dispersions wherein the particles are magnetizable.

These magnetizable particles preferably comprise from 0.5 to 50% (more preferably, from 0.5 to 35% and most preferably, from 0.7 to 20%) by weight of a magnetic filler preferably having a size less than about 1 micron, more preferably between 0.002 and 0.05 micron. The magnetic filler is, of course, sufficiently fine to allow it to be included in the polymer particles.

Exemplary magnetic fillers include:
(i) metals or their alloys (such as iron, iron-silicon, nickel, cobalt or their alloys with molybdenum, chromium, copper, vanadium, manganese, aluminum or titanium),
(ii) iron oxides (such as $Fe_3O_4$ or $\approx\text{-}Fe_2O_3$), in the pure form or in combination with or in mixture with other oxides such as the oxides of cobalt, manganese, zinc, barium or rare earths; and
(iii) chromium dioxide.

The aqueous seeding dispersions of magnetizable particles may be obtained in accordance with the processes described in European Patent No. 38,730 and U.S. Pat. No. 4,157,323, both incorporated herein by reference.

It is particularly preferred to use, as the polymerization initiator, an initiator which is liquid at the temperature at which the first step is carried out (such as dioctanoyl peroxide, didecanoyl peroxide, dioctanoyl peroxidicarbonate, didecyl peroxidicarbonate or didodecyl peroxidicarbonate).

The amount of initiator employed preferably corresponds to about 0.1 to 10%, more preferably about 1 to 5%, by weight relative to the weight of the monomer composition.

The step of diffusing the initiator into the aqueous seeding dispersion may be carried out by bringing the aqueous seeding dispersion into contact, while stirring, with the initiator, the initiator having been preemulsified by homogenization in water containing an emulsifier. This preemulsion may be produced by employing on the order of 200 to 2,000 g of an aqueous solution containing 0.1–0.5% by weight of an emulsifier per 100 g of dry seeding particles.

Exemplary emulsifiers include the alkali metal alkylsulfates, alkylsulfonates and alkylarylsulfonates.

The diffusion step is carried out at a temperature below the decomposition temperature of the initiator, but preferably sufficiently high for the latter to be in the liquid state. This operation is preferably carried out at a temperature on the order of 25° C. to 45° C. for about 15 to 25 hours.

The amphiphilic compounds employed in the second step preferably have an HLB greater than or equal to 10 and less than 20. They may comprise a hydrophilic oligomer block such as, for example, a polyoxyalkylene block comprising from 5 to 100, preferably 5 to 50, $C_2$-$C_3$ oxyalkylene units, or a polycarboxyethylene and/or polyamidoethylene and/or polycyanoethylene block comprising from 4 to 50 carboxyethylene and/or amidoethylene and/or cyanoethylene units. The latter units may have the structure $-[CHR_1-CHR_2]-$, wherein $R_1$ is hydrogen or $R_2$, and $R_2$ is $-COOH$, $-CONH_2$ or $-CN$. The hydrophilic oligomer block is terminated by at least one ion-forming or reactive group.

Exemplary ion-forming or reactive terminal groups include the following:

$-OH$, $-SO_3H$, $-COOH$, $-CHO$, $-\phi CH_2Cl$, $-NH_2$, $-NR_2$, $-NR_3^{\oplus}$(R being a $C_1$-$C_2$—alkyl radical), $-CONH_2$, $-NH-CO-NH-NH_2$, $-SH$ and

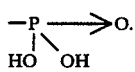

Exemplary amphiphilic compounds may include:

(i) polyoxyethylenated and/or polyoxypropylenated fatty alcohols or fatty acids, having 5 to 50 oxyalkylene units, and in which the hydrophobic block contains about 8 to 20 carbon atoms (such as the CEMULSOL DB products marketed by Societe Francaise d'Organo Synthese, and the SOPROPHOR LA products marketed by Rhone-Poulenc);

(ii) the esters of such polyoxyethylenated and/or polyoxypropylenated fatty alcohols, carrying semicarbazide groups (such as the esters of such polyoxyethylenated and/or polyoxypropylenated fatty alcohols with para-methyl meta-semicarbazide phenylcarbamic acid), or carrying acid groups (such as the monoesters of such polyoxyethylenated and/or polyoxypropylenated fatty alcohols with azelaic acid) or carrying thiol groups (such as the esters of such polyoxyethylenated and/or polyoxypropylenated fatty alcohols with thioglycolic acid);

(iii) the amides of such polyoxyethylenated and/or polyoxypropylenated fatty acids (such as the ETHOMID products marketed by Armour Industrial Chemical Co.);

(iv) polyoxyethylenated and/or polyoxypropylenated alkylphenols having from 5 to 50 oxyalkylene units, and wherein the alkyl radical or radicals contains or contain from 8 to 12 carbon atoms, and their esters with phosphoric acid (such as the SOPROPHOR BC and OP products marketed by Rhone-Poulenc, the SOPROPHOR NFP products marketed by Geronazzo and the GAFAC RE products marketed by General Aniline and Film Corp.); and (v) polyoxyethylenated fatty amines wherein the hydrophobic block contains from 8 to 22 carbon atoms (such as the SOPROMINE products marketed by Rhone-Poulenc and the ETHOMEEN products marketed by Armour Industrial Co.).

The amount of amphiphilic compound employed preferably is such that it represents about $10^{-5}$ to $10^{-1}$ mole, more preferably $10^{-4}$ to $10^{-2}$ mole, per 100 g of final polymer.

The monomer or monomers, as well as the amphiphilic compound, are introduced, with stirring, into the reaction mixture resulting from the first step.

The swelling step preferably takes on the order of $\frac{1}{2}$ to 4 hours, and preferably is carried out at a temperature on the same order as that of the diffusion step.

The third step—that is, the polymerization step—is carried out by raising the temperature to a level at or above the decomposition temperature of the initiator. This polymerization operation preferably takes about 3 to 6 hours.

If an insoluble organic compound other than the initiator has been employed in the first step, it may be removed—for example, by evaporation in vacuo.

The mixture obtained is thus an aqueous dispersion of particles comprising macromolecular chains enmeshed, in their peripheral layer, with the hydrophobic part of the amphiphilic compound, thus fixing the amphiphilic compound to the surface of the particles.

The amphiphilic compound which has not been implanted during the polymerization operation, as well as any emulsifier constituent present beforehand in the dispersion, may subsequently be removed by washing with water—for example, by ultrafiltration.

The polymer particles containing the surface-implanted amphiphilic compound, which are thus obtained, may, if desired, be isolated from the aqueous medium by the conventional methods of sedimentation by centrifuging.

The particles, or latices of these particles, obtained in accordance with the process of the invention are particularly useful in biological applications for fixing biological molecules (such as antibodies and antigens) by covalent bonds.

The fixing of biological molecules by covalent bonds onto the polymer particles can be carried out by a coupling reaction, which reaction involves the terminal groups of the implanted amphiphilic molecule and the functional groups of the biological molecule to be fixed.

The coupling reaction can be carried out in accordance with well-known methods, for example:

resorting to coupling agents (such as glutaraldehyde or a water-soluble carbodiimide), or by activation of the functional groups of the polymer (for example, by diazotization, by the action of cyanogen bromide or of hydrazine), followed by reaction with the molecule to be fixed.

The products can accordingly be used for carrying out diagnostic tests of the agglutination, radioimmunological and enzymatic type.

The examples which follow are illustrative and should not be considered as limiting the scope or spirit of the invention.

EXAMPLE 1

Implantation of CEMULSOL DB 25/18 (abbreviated AC-OH: an amphiphilic compound having an alcohol functional group), as the amphiphilic compound, on polystyrene particles.

Empirical formula of the amphiphilic compound: $C_{18}H_{37}O-CH_2-CH_{250}OH$

The HLB of CEMULSOL DB 25/18 is 17.8. (Methods for determining HLB are found in *Kirk-Othmer, Encyclopedia of Chemical Technology*, 3rd Edition, Volume 8, pp. 910–912, incorporated herein by reference. For example, for CEMULSOL DB 25/18, the % ethylene oxide is divided by 5, yielding the value 17.8 (that is, $[(2200/2470) \times 100 - 5)]$.

316.4 g of water, 1.54 g of dioctanoyl peroxide and 1.12 g of sodium laurylsulfate are introduced into a 500 ml vessel. The mixture is heated at 30° C until the dioctanoyl peroxide has melted. The mixture is then emulsified with an Ultraturrax for 1 minute at 20,000 rpm while keeping the temperature at between 25 and 35° C.

56 g of particles of a seeding latex of polystyrene, having a solids content of 30% by weight and containing calibrated particles of 0.8 micron are added. The whole is stirred for 20 hours at 30° C.

20.44 g of styrene and 7.64 g of amphiphilic compound (corresponding to 3.09 millimoles of amphiphilic compound) are added to the mixture thus prepared. The whole is stirred for 2 hours at 40° C. and 400 rpm.

The temperature is raised to 70° C. This temperature is maintained for 4 hours, while stirring at 70 rpm.

The unreacted styrene is removed by stripping at 70° C. under a pressure of 160 mm Hg in a rotary evaporator.

After cooling, the latex obtained is washed by ultrafiltration, using 2.5 liters of purified water per 10 g of latex particles, so as to remove the non-implanted molecules of amphiphilic compound, as well as the emulsifiers present in the starting latex.

The latex remains stable after ultrafiltration, this being an index of the implantation of the amphiphilic compound.

A determination by nuclear magnetic resonance is carried out on the latex obtained.

It is found that the quantity by weight of amphiphilic compound implanted in 100 g of final particles is 7.8 g (theoretical value=9.1 g).

EXAMPLE 2

Implantation of the ester of CEMULSOL DB 25/18 and of paramethyl meta-semicarbazide phenylcarbamic acid (abbreviated ACSC: amphiphilic compound having a semicarbazide functional group) as the amphiphilic compound, on the particles of a calibrated polystyrene latex.

Empirical formula of the amphiphilic compound:

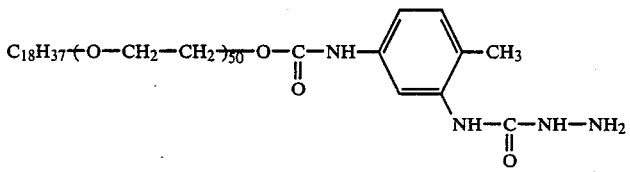

Preparation of the amphiphilic compound

The compound is prepared in two stages:

a first stage, consisting of functionalizing the CEMULSOL DB 25/18 by means of toluene diisocyanate in the presence of dioxane as the solvent, at a temperature of 90° C., and a second stage consisting of functionalizing the CEMULSOL DB 25/18 thus obtained by addition of hydrazine hydrate in the presence of dioxane at ambient temperature.

The desired amphiphilic compound is precipitated cold in diethyl ether.

Implantation

The operation described in Example 1 is repeated, replacing the CEMULSOL DB 25/18 by 7.64 g of its derivative prepared as indicated above, this corresponding to 2.86 millimoles of amphiphilic compound dispersed in the styrene.

The result of the NMR determination is shown in Table I.

EXAMPLE 3

Implantation of the ester of CEMULSOL DB 25/18 and thioglycolic acid (abbreviated AC-SH: amphiphilic compound having a thiol functional group) as the amphiphilic compound, on particles of a calibrated polystyrene latex.

Empirical formula of the amphiphilic compound:

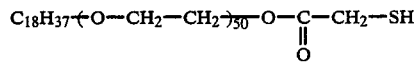

This compound can be prepared in accordance with the process described in U.S. Pat. No. 2,461,920, incorporated herein by reference.

The operation described in Example 1 is repeated, replacing the CEMULSOL DB 25/18 by 7.64 g of its thioglycolic acid ester of the above formula, corresponding to 3.00 millimoles of amphiphilic compound.

The result of the conductimetric determination is shown in Table I.

EXAMPLE 4

Implantation of the monoester of CEMULSOL DB 25/18 and of azelaic acid (abbreviated AC-COOH: amphiphilic compound having an acid functional group), as the amphiphilic compound, on particles of a calibrated polystyrene latex.

Empirical formula of the amphiphilic compound:

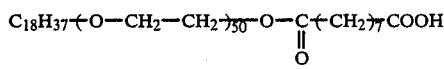

This compound can be prepared by esterification of CEMULSOL DB 25/18 with azelaic acid in pyridine in the presence of dicyclohexylcarbodiimide as the condensation agent.

The operation described in Example 1 is repeated, replacing the CEMULSOL DB 25/18 by 3.82 g of its ester of the above formula, this corresponding to 1.44 millimoles of amphiphilic compound.

The result of the NMR determination is shown in Table I.

EXAMPLE 5

Implantation of CEMULSOL DB 25/18 as the amphiphilic compound on calibrated particles of a 40/60, by weight, copolymer of styrene and methyl methacrylate.

The operation described in Example 1 is repeated, replacing, weight for weight, the polystyrene seeding latex (56 g of particles) by a seeding latex of a 40/60, by weight, copolymer of styrene and methyl methacrylate (56 g of particles) having a solids content of 33% and consisting of calibrated particles of 0.705 micron.

The nature and quantities of the other reactants employed are the same as those in Example 1 (that is, 20.44 g of styrene are employed in the monomer composition). The working conditions are also the same as in Example 1.

The result of the NMR determination is shown in Table I.

EXAMPLE 6

The latex particles obtained in Example 1 are sedimented by means of a BECKMANN L 50 centrifuge equipped with a rotor 30 (apparatus marketed by BECKMANN) revolving at 10,000 rpm for 15 minutes, and are then dried in a vacuum oven at 40° C. and stored under nitrogen.

The properties of the particles are preserved.

The abbreviations relating to the starting polymer shown in the table have the following meaning:
PS: polystyrene
P(S/MMA): styrene/methyl methacrylate copolymer
SC: solids content
S denotes styrene.

In Table I, "% Implanted" denotes weight % amphiphilic compound, relative to the weight of the final polymer implanted with amphiphilic compound.

TABLE I

| EXAMPLE | 1 | 2 | 3 | 4 | 5 |
|---|---|---|---|---|---|
| LATEX | | | | | |
| polymer | PS | PS | PS | PS | P(S/MMA) |
| ∅ micron | 0.8 | 0.8 | 0.8 | 0.8 | 0.705 |
| SC % | 30 | 30 | 30 | 30 | 33 |
| MONOMER | S | S | S | S | S |
| AMPHIPHILIC COMPOUND | | | | | |
| nature | AC—OH | ACSC | AC—SH | AC—COOH | AC—OH |
| g/100 g of polymer + monomer | 10 | 10 | 10 | 5 | 10 |
| mole/100 g of polymer + monomer | $4.05 \times 10^{-3}$ | $3.74 \times 10^{-3}$ | $3.93 \times 10^{-3}$ | $1.89 \times 10^{-3}$ | $4.05 \times 10^{-3}$ |
| % Implanted | | | | | |
| theoretical | 9.1 | 9.1 | 9.1 | 4.8 | 9.1 |
| determined | 7.8 | 7.9 | 5.2 | 3.3 | 7.2 |

We claim:

1. A process for the preparation of an aqueous dispersion of polymer particles possessing, implanted on their surface, amphiphilic molecules carrying ion-forming or reactive groups, comprising the following steps:
   (1) diffusing, into a previously prepared aqueous seeding dispersion of polymer particles, an organosoluble polymerization initiator having a solubility in water of from about $10^{-3}$ to $10^{-2}$ g/liter of water, said diffusion being carried out at a temperature below the decomposition temperature of said initiator;
   (2) swelling said particles of said dispersion thus obtained by introducing a monomer composition comprising (a) at least one monomer and (b) at least one amphiphilic compound having an HLB greater than or equal to 10 and a molecular weight greater than or equal to 400, wherein the hydrophilic block of said amphiphilic compound is a hydrophilic oligomer block terminated by at least one ion-forming or reactive group, said swelling being carried out by the monomer component (a) with a quantity of monomer composition less than the maximum quantity of said composition which said seeding dispersion can absorb, at a temperature below the decomposition temperature of said initiator; and
   (3) polymerizing said at least one monomer of said monomer composition at a temperature at least equal to the decomposition temperature of said initiator, the nature of said seeding polymer and the nature of said at least one monomer of said monomer composition, being such that the final polymer has a glass transition temperature Tg above about 40° C., said polymerzation resulting in the implantation of said amphiphilic compound (b) of the monomer composition in the surface layer of the polymer particles.

2. The process of claim 1, comprising the further step of removing at least a portion of any amphiphilic compound not implanted on the surface of said aqueous dispersion particles obtained in said step (3).

3. The process of claim 1, comprising the further step of isolating the polymer particles obtained in said step (3), said particles possessing molecules of said amphiphilic compound implanted on their surface.

4. The process of claim 2, comprising, subsequent to said removal of at least a portion of said amphiphilic compound, the further step of isolating said particles obtained after said removal step, said particles possessing molecules of said amphiphilic compound implanted on their surface.

5. The process of claim 1, wherein said seeding polymer comprises units derived from vinylaromatic monomers, alkyl esters of α, β-unsaturated acids, unsaturated esters of carboxylic acids, vinyl chloride, vinylidene chloride, dienes or monomers possessing nitrile functional groups.

6. The process of claim 1, wherein said monomer or monomers polymerized in said polymerization step (3) are vinylaromatic monomers, alkyl esters of α, β-unsaturated acids, unsaturated esters of carboxylic acids, vinyl chloride, vinylinene chloride, dienes or monomers possessing nitrile functional groups.

7. The process of claim 1, wherein said aqueous seeding dispersion has a solids content of from about 1 to 40% by weight, and comprises particles having a diameter of from about 0.1 to 15 microns.

8. The process of claim 1, wherein said seeding polymer represents from 50 to 95% by weight of the final polymer obtained in said step (3).

9. The process of claim 1, wherein said particles of said aqueous seeding dispersion are magnetizable.

10. The process of claim 1, wherein said initiator is dioctanoyl, peroxide, didecanoyl peroxide, dioctanoyl peroxidicarbonate, didecyl peroxidicarbonate or didodecyl peroxidicarbonate.

11. The process of claim 1, wherein the quantity of said initiator employed corresponds to about 0.1 to 10% by weight relative to the weight of said monomer composition.

12. The process of claim 1, wherein said diffusion step (1) is carried out by bringing said aqueopus seeding dispersion into contact, while stirring, with said initiator, said initiator having been preemulsified by homogenization in water containing an emulsifier.

13. The process of claim 1, wherein said diffusion step (1) is carried out at a temperature which is below the decomposition temperature of said initiator, but is sufficiently high for said initiator to be in the liquid state.

14. The process of claim 1, wherein said amphiphilic compound comprises a hydrophilic polyoxyalkylene oligomer block comprising from 5 to 100 $C_2$-$C_3$ oxyalkylene units or a hydrophilic polycarboxyethylene and/or polyamidoethylene and/or polycyanoethylene oligomer block comprising from 4 to pb 50 carboxyethylene and/or amidoethylene and/or cyanoethylene units, said hydrophilic oligomer block being terminated by at least one —OH, —SO$_3$H, —COOH, —CHO, —$\phi$CH$_2$Cl, —NH$_2$, —NR$_2$, —NR$_3^\oplus$(R being a $C_1$-$C_2$—alkyl radical), —CONH$_2$, —NH—NH$_2$, —NH—CO—NH—NH$_2$, —SH, or

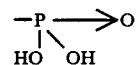

group.

15. The process of claim 1, wherein the quantity of said amphiphilic compound employed is such that it represents about $10^{-5}$ to $10^{-1}$ mole per 100 g of final polymer.

16. The process of claim 1, wherein said swelling step (2) is carried out at a temperature on the same order as that of said diffusion step (1).

17. The process of claim 1, wherein said polymerization step (3) is carried out at a temperature above the decomposition temperature of said initiator.

18. A method of using the polymer particles obtained by the process of claim 3, wherein said particles are employed in a biological application.

19. A method of using the dispersion of polymer particles obtained by the process of claim 1, wherein said dispersion is employed in a biological application.

* * * * *

UNITED STATES PATENT AND TRADEMARK OFFICE
CERTIFICATE OF CORRECTION

PATENT NO.  : 4,929,662
DATED       : May 29, 1990
INVENTOR(S) : Roger Hogenmuller et al.

It is certified that error appears in the above-identified patent and that said Letters Patent is hereby corrected as shown below:

Claim 12, Column 9, Line 12, "aqueopus" should be --aqueous--;

Claim 14, Column 9, Line 25, "4 to pb 50" should be --4 to 50--.

Signed and Sealed this

Fifteenth Day of September, 1992

Attest:

DOUGLAS B. COMER

*Attesting Officer*    *Acting Commissioner of Patents and Trademarks*